United States Patent [19]

Peppel et al.

[11] Patent Number: 5,730,150
[45] Date of Patent: Mar. 24, 1998

[54] GUIDEWIRE DISPENSER

[75] Inventors: Peter W. Peppel, Nazareth; William J. Reiser, Bethlehem, both of Pa.

[73] Assignee: B. Braun Medical Inc., Bethlehem, Pa.

[21] Appl. No.: 587,291

[22] Filed: Jan. 16, 1996

[51] Int. Cl.⁶ ........................................ A61B 5/00
[52] U.S. Cl. ........................................ 128/772
[58] Field of Search ........................ 128/657, 658, 128/722; 604/159, 171

[56] References Cited

U.S. PATENT DOCUMENTS

| | | | |
|---|---|---|---|
| 4,860,757 | 8/1989 | Lynch et al. | 128/657 |
| 5,125,416 | 6/1992 | Phillips | 128/772 |
| 5,125,906 | 6/1992 | Fleck | 604/171 |
| 5,366,444 | 11/1994 | Martin | 604/159 |
| 5,438,993 | 8/1995 | Lynch et al. | 128/657 |
| 5,484,419 | 1/1996 | Fleck | 604/171 |
| 5,507,300 | 4/1996 | Mukai et al. | 128/772 |

FOREIGN PATENT DOCUMENTS

| | | |
|---|---|---|
| 0587984 | 5/1993 | European Pat. Off. |
| 207358 | 12/1967 | U.S.S.R. |

*Primary Examiner*—Max Hindenburg
*Attorney, Agent, or Firm*—Hopgood, Calimafde Kalil & Judlowe L.L.P.

[57] ABSTRACT

A catheter guidewire dispenser is provided for inserting a guidewire into a blood vessel. The dispenser houses the guidewire in an interior coiled path having spaced apart protrusions which provide friction against the guidewire to retain it within the housing. The device is made from a material with a high coefficient of friction. Single-piece construction prevents disassembly and damage during transit, storage and use. An advancement mechanism having a ribbed surface provides improved feeding control of the guidewire.

13 Claims, 4 Drawing Sheets

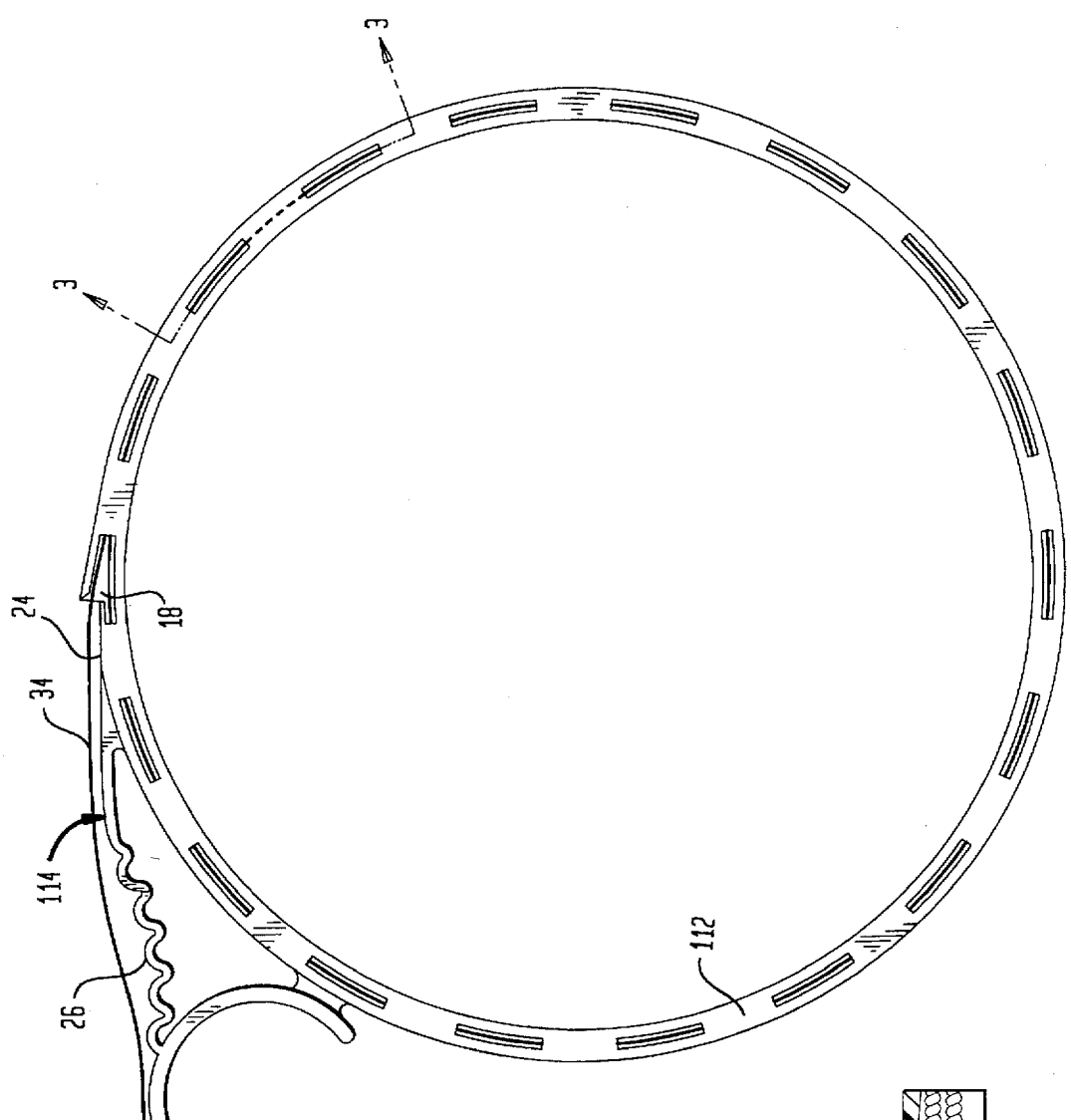
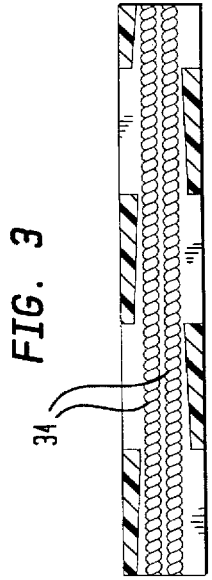
FIG. 2
FIG. 3

GUIDEWIRE DISPENSER

FIELD OF THE INVENTION

The present invention relates to a dispenser for a catheter guidewire. In particular, the present invention is directed to a single-piece apparatus for facilitating sterile insertion of a guidewire into a blood vessel or body cavity.

BACKGROUND OF THE INVENTION

A commonly used technique for inserting a catheter into a blood vessel, referred to as the Seldinger technique, involves inserting a hollow needle to puncture the blood vessel, inserting a thin guidewire into the vessel through the hollow needle, removing the needle, guiding the catheter over the guidewire into the blood vessel and, finally, removing the guidewire.

The flexible guidewires are generally made of coiled springs tightly wrapped around a core wire. Some, known as "J" guidewires, have a J-shaped, flexible tip to aid in guiding the wire to the desired vessel. Guidewires are generally packaged in a dispenser made up of a coiled tube. Several prior art devices for one-handed insertion of these guidewires are known, such as those disclosed in U.S. Pat. Nos. 4,860,757 and 5,438,993 to Lynch, U.S. Pat. No. 5,125,906 to Fleck and U.S. Pat. No. 5,366,444 to Martin.

Existing dispensers suffer from problems arising during shipment or storage. These devices typically are assembled from multiple components, including an advancement mechanism for feeding the guidewire into the blood vessel and a coiled tube which is attached to one end of the advancement mechanism for storing the guidewire safely before use. Plastic clips are usually provided to keep the tubes from uncoiling. Due to the compressive force on the coiled tube, the components of these dispensers tend to separate during shipment and storage. Particularly, the tube will dislodge from the clips or the advancement mechanism. This often results in a bending of the enclosed guidewire, rendering the wire unusable. If the dispenser comes apart during use, the guidewire may fall to the floor or otherwise be exposed to non-sterile conditions.

The coiled tubes which store the guidewires are generally fabricated of polyethylene, a slippery material with a low coefficient of friction. In these devices, the guidewire slides freely within the hollow chamber of the solid-walled tube and sometimes slips completely out of the dispenser during transit. This again, leads to bent guidewires, or exposure to a non-sterile environment.

Prior art dispensers also have problems related to their handling during actual use. Most of the known devices have some sort of opening in the advancement mechanism or tubing so that an operator's gloved fingers can apply pressure to the guidewire, advancing the guidewire into the blood vessel. But, the prior art devices typically have round tubes which tend to slip in the operator's hand. Moisture or fluids on the operator's fingers can also cause slippage between the fingers and the guidewire, making advancement of the guidewire more difficult. Because these dispensers are used in a variety of positions and procedures, it is important that the operator have sufficient tactile control of the dispenser at all times.

As previously indicated, bent guidewires cannot be used. Guidewires are occasionally bent during the manufacturing process or during assembly of the dispenser. It is preferable to screen these defective guidewires prior to distribution, however, none of the prior art dispensers have any mechanism for preventing assembly of defective guidewires.

It is therefore an object of the present invention to provide an improved guidewire dispenser of one-piece construction to eliminate the possibility of components separating during shipment and use.

It is another object of the invention to provide a dispenser which suitably holds and protects a guidewire from premature discharge during shipment and use.

It is a further object of the invention to provide a dispenser which minimizes slippage between the guidewire and the operator's fingers during advancement of the guidewire.

It is still a further object of the invention to provide a guidewire dispenser with improved tactile control for ease of handling.

It is yet a further object of the present invention to provide a dispenser which facilitates the detection of defective guidewires during assembly.

Accordingly, the present invention is directed to a guidewire dispenser fabricated from a single piece ring for facilitating insertion of a guidewire into a blood vessel. The device of the present invention securely holds a guidewire in place within an interior coiled path during shipment and storage, without interfering with advancement of the guidewire during end-use application. The device of the present invention is shaped to increase tactile control with an advancement mechanism to prevent slippage of the guidewire. The device also prohibits loading of a guidewire with damaged ends.

SUMMARY OF THE INVENTION

In accordance with the present invention, a dispenser for inserting a catheter guidewire into a blood vessel is disclosed. The disclosed apparatus comprises a single piece housing having an interior coiled path for retaining a guidewire in a series of loops and a guidewire advancement mechanism, integrally molded with the housing, for conveying the guidewire from an aperture in the housing to the blood vessel. The disclosed device is thus designed as a single-piece dispenser to avoid separation of individual components.

In another of its aspects, the invention provides a device having spaced-apart protrusions along the length of the interior coiled path. These protrusions intermittently engage the guidewire, preventing the guidewire from premature discharge from the housing during shipment.

In yet another of its aspects, the invention provides a guidewire advancement mechanism having a platform with a ribbed surface for removing fluids from an operator's fingers. The disclosed device provides improved tactile control for feeding the guidewire into the blood vessel.

Another aspect of the disclosed invention provides a plurality of spaced-apart openings along the interior coiled path for laterally displacing a bent guidewire from the interior coiled path during assembly. The disclosed device provides increased quality control by screening out damaged guidewires before distribution.

BRIEF DESCRIPTION OF THE DRAWINGS

The invention will be further described in connection with the accompanying drawings, in which:

FIG. 2 is a view of an alternative embodiment of the guidewire dispenser;

FIG. 3 is a sectional view of the device along line 3—3 of FIG. 2;

DETAILED DESCRIPTION OF THE INVENTION

Figure 1:
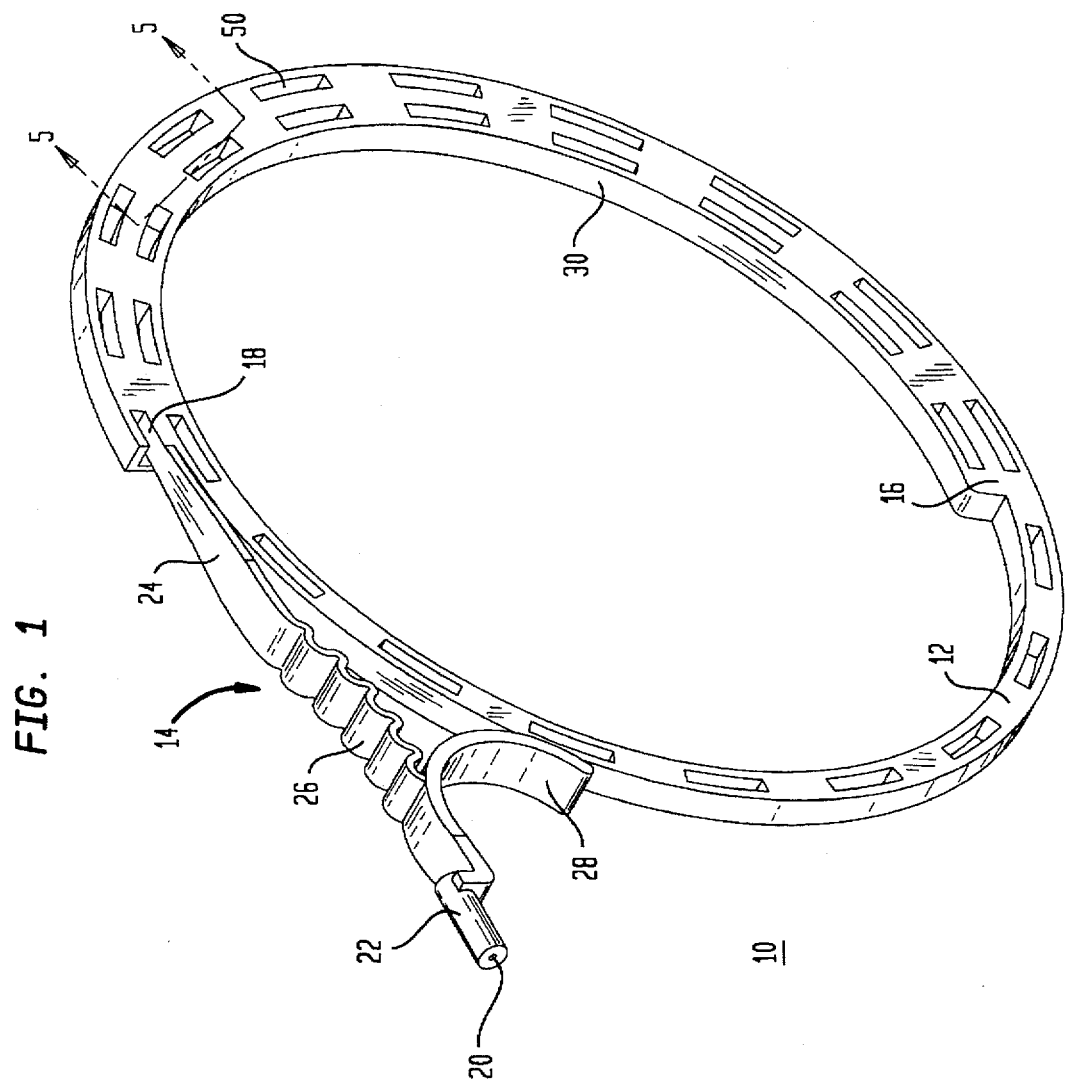
FIG. 1 is a general view of a guidewire dispenser constructed in accordance with the invention.

A first embodiment of the catheter guidewire dispenser 10 is illustrated in FIG. 1. In general, the dispenser is constructed from a single-piece injection-molded housing 12 having a ring shape with an integrally molded wire advancement mechanism 14. The housing 12 houses a guidewire (not shown) in a series of multi-tiered loops which prevent one portion of the wire from contacting any other portion. In FIG. 1, a two-tiered loop 16 is shown, but additional tiers may be used to accommodate longer guidewires. Thus, the guidewire is stored within housing 12 in an interior coiled path consisting of a series of overlapping concentrically coiled or spiralling loops.

Aperture 18 located in housing 12 adjacent to one end of advancement mechanism 14 allows the guidewire to exit tangentially to the housing. The guidewire then passes over advancement mechanism 14 and through hollow bore 20 in dispenser tip 22.

Advancement mechanism 14 may consist of flat platform 24 and/or ribbed surface 26. These regions are exposed to allow the user's fingers to access the guidewire so that it can be manually advanced into a blood vessel.

Entire dispenser 10 is injection molded to form a single piece apparatus, leaving no detachable components during use, shipment or storage of the device. A single piece apparatus is also advantageous because there are no costs associated with assembly of a multi-piece device; and multiple components are not required as inventory.

The dispenser is preferably molded using a thermoplastic resin. Suitable resins include polycarbonate, styrene butadiene, methyl methacrylate, acrylonitrile butadiene styrene, and combinations of the above. Prior art dispensers were generally made of polystyrene. Although this is an acceptable material, it is preferable to use a resin having a coefficient of static friction greater than about 0.30, so that the guidewire will have less tendency to prematurely eject from the housing. This added friction should be sufficient to keep the guidewire from sliding too freely so that it dislodges from the housing, but low enough so that placement of a guidewire is not impeded.

FIG. 2 shows a single-tiered embodiment of guidewire dispenser 110. In this embodiment, only single-tiered housing 112 is employed. If guidewires longer than the circumference of the ring are required, guidewire 34 doubles up on itself within the interior coiled path as shown in the cross-sectional view illustrated by FIG. 3. In this embodiment, guidewire 34 may contact its own surface at various points and the width of the housing may be increased to accommodate side-by-side wire lengths.

Again referring to FIG. 2, alternative advancement mechanism 114 is shown. In this embodiment, flat platform 24 and ribbed surface 26 are offset from one another so that aperture 18 and bore hole 20 in dispenser tip 22 are not coaxial. Guidewire 34 is diverted from a straight line path in the vicinity of the advancement mechanism, whereby a braking effect is exerted to retain guidewire 34 within housing 112. This alternative advancement mechanism may be used in conjunction with the multi-tiered embodiment as well.

The operation of device 10 (or 110) will now be described with reference to FIG. 4 which illustrates device 10 as held in a user's hand 40. Index finger 42 of the user's hand engages finger grip 28 of dispenser 10. Thumb 44 rests atop guidewire 34 in the exposed region above advancement mechanism 14. The user's remaining fingers are curled around housing 12 so that the user maintains a firm controlling grasp of the dispenser. Previously used tubular or round dispenser casings tended to slip in the user's hand causing loss of control. To avoid this, at least inner surface 30 (FIG. 1) of housing 12 is flat to improve the user's grasp of the device. Preferably, the ring shaped housing as a whole has a non-round cross-section for improved control.

Figure 4:
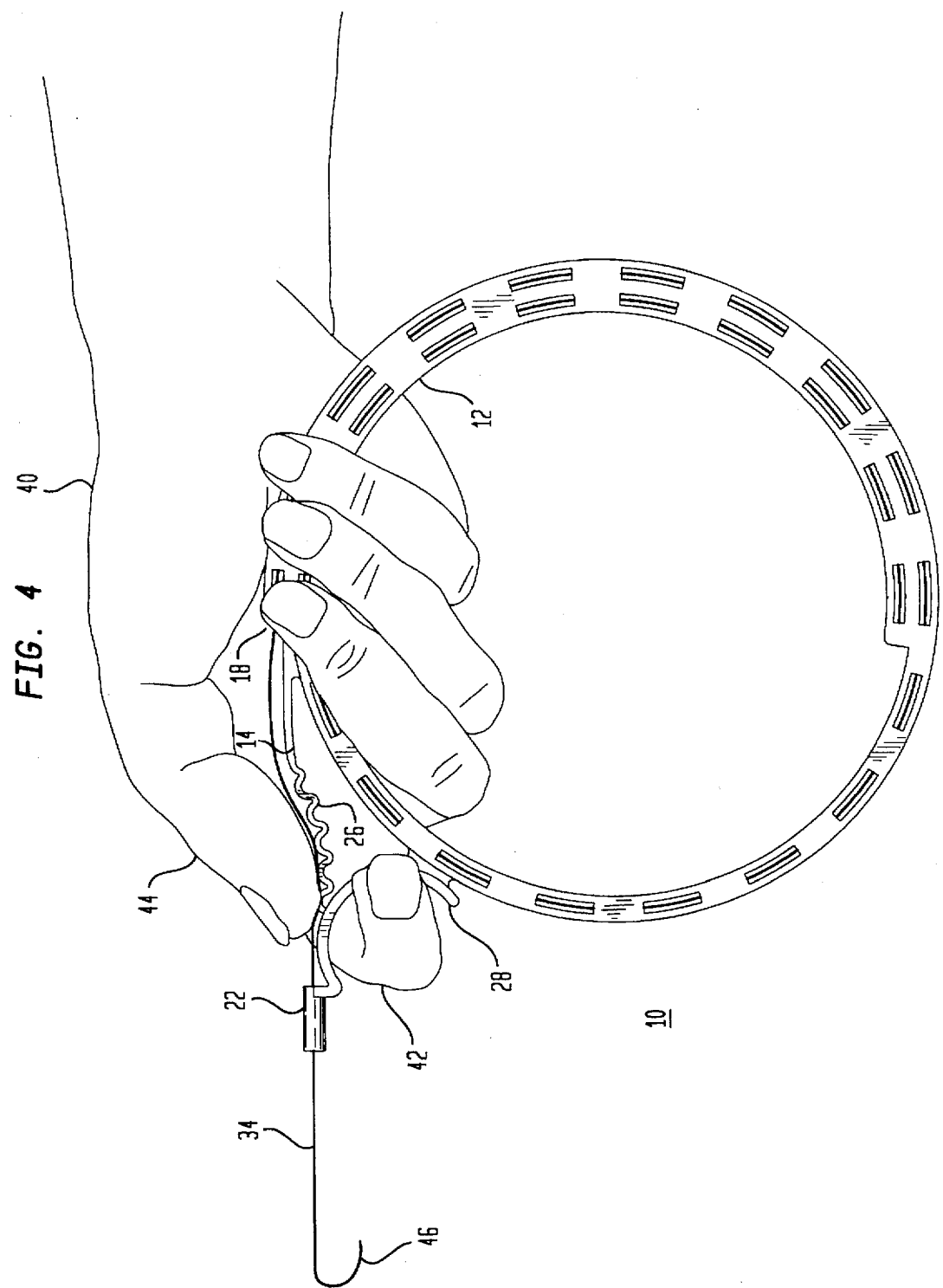
FIG. 4 is a view showing the device during end-use application.

To insert the guidewire into a blood vessel, the user grasps dispenser 10 as shown in FIG. 4 with thumb 44 resting on guidewire 34 close to aperture 18. Applying pressure to the guidewire, the user advances the thumb toward dispenser tip 22, pulling the guidewire out of housing 12 at aperture 18 and drawing it over advancement mechanism 14 through the bore hole in tip 22 where it is fed through a vascular access needle into the patient's blood vessel. Raising the thumb and retracting it to the starting position allows the user to repeat the above cycle until guidewire 34 is fully withdrawn from dispenser 10. If the guidewire has J-shaped tip 46, as illustrated in FIG. 4, the user may start by placing the thumb at tip end 22 of advancement mechanism 14 and moving the thumb in the reverse direction. This action will retract the J-shaped end of the guidewire into tip 22, straightening it before insertion into the needle and the blood vessel.

In typical usage of a guidewire dispenser, the physician's or user's gloved fingers are often wet from moisture or other fluids. This often causes the thumb to lose its grip against the guidewire, whereby the guidewire may not advance in concert with the motion of the thumb. As shown in FIGS. 1, 2 and 4, advancement mechanism 14 is partially comprised of ribbed surface portion 26. The ridges act to remove this moisture from the thumb and provide better contact between the user's thumb and the guidewire.

Figure 5:
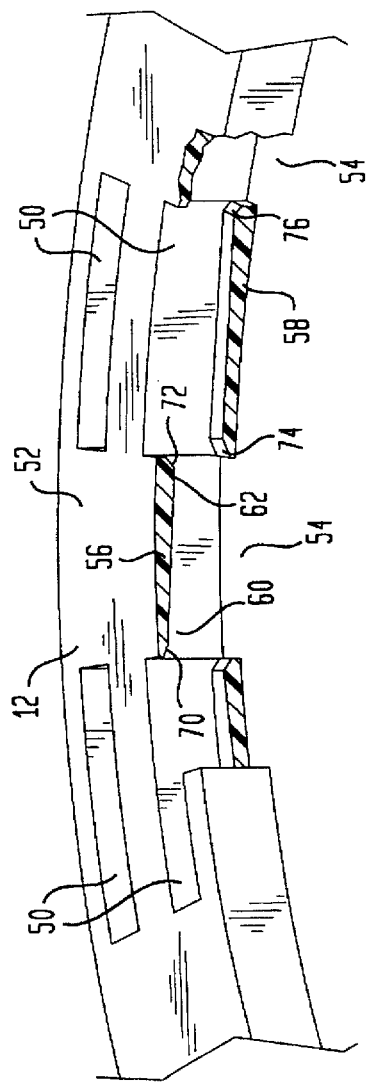
FIG. 5 is a cut-away view along line 5—5 of FIG. 1.

As a further aid to keep the guidewire from prematurely ejecting from the housing during transit, a series of stepped protrusions are molded into the interior coiled path as illustrated by FIG. 5, which is a cut-away view taken along line 5—5 of FIG. 1. Housing 12 has a series of spaced-apart openings 50 along one side. Any number of openings may be used. In space 52 between openings 50 there is solid wall material. The opposing side of housing 12 has openings 54 (opposite wall material 52). Thus, there are alternating openings 50, 54 in two opposing sides of the housing. The purpose of these holes will be described below.

Protrusion 56 is opposite opening 54 and protrusion 58 is opposite opening 50. These stepped protrusions intermittently engage the guidewire to produce additional friction as the guidewire slides along the interior coiled path, thereby preventing the wire from slipping out of the housing unless the user is applying forward pressure on the wire at the advancement mechanism. Protrusions 56 and 58 may be tapered (i.e., larger at end 62 than at end 60) so that a guidewire is easily directed along the interior coiled path during loading. The edges of the stepped protrusions may also be further tapered as shown at points 70, 72, 74 and 76 to prevent the guidewire from catching on the protrusions when sliding in either direction.

Figure 6:
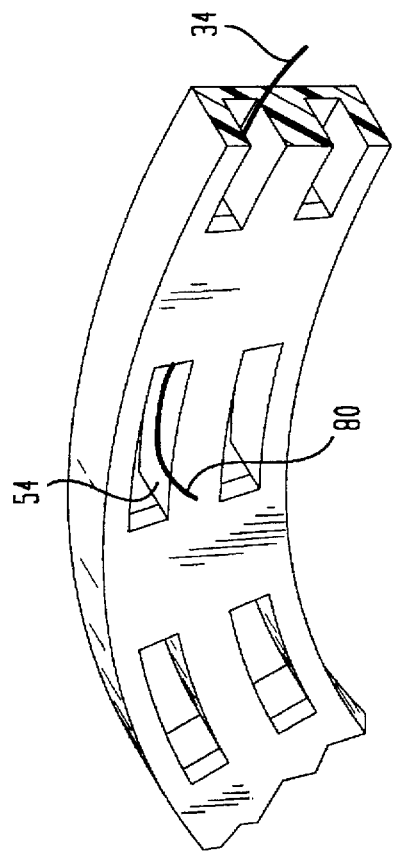
FIG. 6 is an enlarged partial view of the guidewire dispenser of the present invention.

Referring to FIG. 6, the defective guidewire screening feature is illustrated. Guidewire 34 is initially loaded into the dispenser by inserting the straight end of the guidewire into bore hole 20 in dispenser tip 22 (FIG. 1). The guidewire is further inserted until it enters aperture 18 (FIG. 1) whereupon it enters the interior coiled path for storage. If the end of the guidewire has been damaged or bent during manufacture or assembly, bent end 80 will exert pressure on the inner walls of the interior coiled path. At some point, bent end 80 will be laterally displaced through openings 50 or 54, prohibiting further loading of the damaged guidewire. As a result, an assembly technician is alerted to discard the defective guidewire before it is distributed.

Various modifications and alterations to the present invention may be appreciated based on a review of this disclosure. These changes and additions are intended to be within the scope and spirit of this invention as defined by the following claims.

What is claimed is:

1. A catheter guidewire dispenser for inserting a guidewire into a blood vessel, the dispenser comprising:

a housing having an interior coiled path for retaining said guidewire in sliding engagement within said housing and an aperture for dispensing said guidewire, said interior coiled path having a plurality of spaced-apart protrusions for intermittently engaging said guidewire; and a guidewire advancement mechanism operatively coupled to said housing proximate to said aperture, for conveying said guidewire from said housing to said blood vessel whereby the intermittent engagement between said guidewire and said protrusions adds resistance to the sliding engagement of said guidewire within said housing, preventing premature discharge of said guidewire.

2. The guidewire dispenser of claim 1, wherein said protrusions are tapered.

3. The guidewire dispenser of claim 1, wherein said housing is molded of a thermoplastic resin having a coefficient of static friction greater than about 0.30.

4. The guidewire dispenser of claim 1, wherein said housing is molded of a thermoplastic resin selected from the group consisting of polycarbonate, styrene butadiene, methyl methacrylate, acrylonitrile butadiene styrene and combinations thereof.

5. The guidewire dispenser of claim 1, wherein the guidewire advancement mechanism comprises:

a dispenser tip for straightening said guidewire as it is dispensed from said aperture;

a platform underlying said guidewire and extending substantially between said dispenser tip and said aperture, providing an access area to an operator's fingers in order to manually advance said guidewire, at least a portion of said platform having a ribbed surface for removing fluids from said operator's fingers.

6. The guidewire dispenser of claim 1, wherein said housing further comprises a flat external surface adjacent an operator's hand for holding and supporting the guidewire dispenser without slippage.

7. A catheter guidewire dispenser for inserting a guidewire into a blood vessel, the dispenser comprising:

a guidewire housing having an interior coiled path for retaining said guidewire in a series of loops, said housing having an aperture for loading and dispensing said guidewire tangentially to said interior coiled path, said housing also having a plurality of spaced-apart openings along said interior coiled path for laterally displacing a bent guidewire from said interior coiled path during said loading; and a guidewire advancement mechanism operatively coupled to said housing proximate to said aperture, for conveying said guidewire from said housing to said blood vessel.

8. A catheter guidewire dispenser for inserting a guidewire into a blood vessel, the dispenser comprising:

a guidewire housing having an interior coiled path for retaining said guidewire in a continuous spiraling loop, said housing having an aperture for dispensing said guidewire tangentially to said housing;

a guidewire advancement mechanism, operatively coupled to said housing proximate to said aperture, for conveying said guidewire from said housing to said blood vessel;

the housing being molded as a single piece having a first plurality of openings, separated by spaces, along one side of said housing and a second plurality of openings, opposite said spaces, in an opposing side of said housing.

9. The guidewire dispenser of claim 8, wherein the guidewire advancement mechanism comprises:

a dispenser tip; and a platform underlying said guidewire and extending substantially between said dispenser tip and said aperture, providing an access area to an operator's fingers in order to manually advance said guidewire, at least a portion of said platform having a ribbed surface for removing fluids from said operator's fingers.

10. The guidewire dispenser of claim 8, wherein said housing further comprises a flat external surface adjacent an operator's hand for holding and supporting the guidewire dispenser without slippage.

11. A catheter guidewire dispenser for inserting a guidewire into a blood vessel, the dispenser comprising:

a single-piece, molded guidewire housing having an interior coiled path for retaining said guidewire in a series of spiralling loops, said housing having an aperture for dispensing said guidewire tangentially to said housing; and a guidewire advancement mechanism, integrally molded with and attached to said housing proximate to said aperture, for conveying said guidewire from said housing to said blood vessel.

12. The guidewire dispenser of claim 11 wherein the guidewire advancement mechanism comprises:

a dispenser tip for straightening said guidewire as it is dispensed from said aperture;

a platform underlying said guidewire and extending substantially between said dispenser tip and said aperture, providing an access area to an operator's fingers in order to manually advance said guidewire, at least a portion of said platform having a ribbed surface for removing fluids from said operator's fingers.

13. The guidewire dispenser of claim 11, wherein said housing further comprises a flat external surface adjacent an operator's hand for holding and supporting the guidewire dispenser without slippage.

* * * * *